(12) United States Patent
Nino et al.

(10) Patent No.: US 11,203,102 B2
(45) Date of Patent: Dec. 21, 2021

(54) GEARLESS IN-LINE TORQUE LIMITED DEVICE

(71) Applicant: ECA Medical Instruments, Newbury Park, CA (US)

(72) Inventors: John Nino, Simi Valley, CA (US); David Ivinson, Camarillo, CA (US); David Tory, Simi Valley, CA (US)

(73) Assignee: ECA Medical Instruments, Thousand Oaks, CA (US)

( * ) Notice: Subject to any disclaimer, the term of this patent is extended or adjusted under 35 U.S.C. 154(b) by 462 days.

(21) Appl. No.: 15/946,246

(22) Filed: Apr. 5, 2018

(65) Prior Publication Data

US 2018/0222023 A1  Aug. 9, 2018

Related U.S. Application Data

(63) Continuation of application No. PCT/US2016/055798, filed on Oct. 6, 2016, which is
(Continued)

(51) Int. Cl.
  *B25B 23/147* (2006.01)
  *B25B 23/14* (2006.01)
  (Continued)

(52) U.S. Cl.
  CPC ........ *B25B 23/147* (2013.01); *A61B 17/8875* (2013.01); *B25B 21/007* (2013.01);
  (Continued)

(58) Field of Classification Search
  CPC . B25B 23/141; B25B 23/147; B25B 23/1427; B25B 21/007; A61B 17/007; A61B 2090/031
  (Continued)

(56) References Cited

U.S. PATENT DOCUMENTS 3,695,059 A   10/1972   Laubach
3,998,112 A   12/1976   Pierrat
(Continued)

FOREIGN PATENT DOCUMENTS

DE   2427352 A1   12/1975
EP   1110512 A1   6/2001
(Continued)

OTHER PUBLICATIONS

International Patent Application No. PCT/US2016/054940; Int'l Written Opinion and Search Report; dated Feb. 3, 2017; 12 pages.
(Continued)

*Primary Examiner* — David B. Thomas
*Assistant Examiner* — Thomas Raymond Rodgers
(74) *Attorney, Agent, or Firm* — Ferguson Case Orr Paterson

(57) ABSTRACT

A power driven in-line disposable torque-limiting device having a gearless clutch assembly with a first clutch element affixed to the cylindrical body, a second clutch element engaged with a shaft for rotation together with the shaft, one or more bearing elements disposed between the first clutch element and the second clutch element, and a compressive element configured to apply force across the clutch elements. The first clutch element and second clutch element exert compressive force, shearing force, or both on the one or more bearing elements to provide clutch functionality at predetermined torque limits.

11 Claims, 15 Drawing Sheets

Related U.S. Application Data a continuation of application No. PCT/US2016/054940, filed on Sep. 30, 2016, application No. 15/946,246, which is a continuation of application No. PCT/US2016/035712, filed on Jun. 3, 2016.

(60) Provisional application No. 62/345,607, filed on Jun. 3, 2016, provisional application No. 62/238,359, filed on Oct. 7, 2015, provisional application No. 62/238,354, filed on Oct. 7, 2015, provisional application No. 62/238,419, filed on Oct. 7, 2015.

(51) Int. Cl.

| | | |
|---|---|---|
| *B25B 23/142* | (2006.01) | |
| *A61B 17/88* | (2006.01) | |
| *B25B 21/00* | (2006.01) | |
| *A61B 90/00* | (2016.01) | |

(52) U.S. Cl.
CPC ........ *B25B 23/141* (2013.01); *B25B 23/1427* (2013.01); *A61B 2090/031* (2016.02)

(58) Field of Classification Search
USPC .......................... 81/467; 464/41, 30; 408/140
See application file for complete search history.

(56) References Cited

U.S. PATENT DOCUMENTS

| | | | |
|---|---|---|---|
| 4,177,695 | A | 12/1979 | Grove |
| 4,316,439 | A | 2/1982 | Tyree |
| 4,643,047 | A | 2/1987 | Distin |
| 4,829,851 | A | 5/1989 | Imase |
| 4,922,781 | A | 5/1990 | Peiji |
| 5,145,468 | A | 9/1992 | Nagabhusan |
| 5,180,042 | A | 1/1993 | Ogiso |
| 5,197,930 | A | 3/1993 | Imase |
| 5,683,323 | A | 11/1997 | Imase |
| 6,132,435 | A | 10/2000 | Young |
| 6,487,943 | B1 | 12/2002 | Jansson et al. |
| 6,745,812 | B1 | 6/2004 | Liu |
| 7,766,750 | B2 | 8/2010 | Campbell et al. |
| 7,938,046 | B2 | 5/2011 | Nino |
| 8,157,691 | B2 | 4/2012 | Stanovskoy |
| 8,162,790 | B2 | 4/2012 | Imase |
| 8,221,431 | B2 | 7/2012 | Chenaux |
| 8,365,641 | B2 | 2/2013 | Daglow |
| 9,241,751 | B2 | 1/2016 | Nino |
| 10,131,040 | B2 | 11/2018 | Nino |
| 10,343,269 | B2 | 7/2019 | Nino |
| 10,422,414 | B2 | 9/2019 | Ho |
| 10,610,429 | B2 | 4/2020 | Heneveld, Jr. |
| 2006/0016300 | A1 | 1/2006 | Bubel |
| 2007/0289391 | A1 | 12/2007 | Gao |
| 2008/0015034 | A1 | 1/2008 | Downey |
| 2010/0179560 | A1 | 7/2010 | Chenaux |
| 2010/0216585 | A1 | 8/2010 | Imase |
| 2011/0000347 | A1 | 1/2011 | Stark |
| 2011/0061500 | A1* | 3/2011 | Huang ............... F16D 7/10 81/474 |
| 2012/0031261 | A1 | 2/2012 | Gagnon et al. |
| 2012/0055296 | A1 | 3/2012 | Landowski |
| 2013/0199345 | A1 | 8/2013 | Nino et al. |
| 2013/0226192 | A1 | 8/2013 | Nino et al. |
| 2013/0305889 | A1 | 11/2013 | Nino et al. |
| 2014/0000420 | A1 | 1/2014 | Chuang et al. |
| 2015/0148175 | A1 | 5/2015 | Kierspe |
| 2015/0151416 | A1 | 6/2015 | Chen |
| 2015/0321326 | A1 | 11/2015 | Nino et al. |
| 2016/0184043 | A1 | 6/2016 | Ivinson |
| 2017/0232592 | A1 | 8/2017 | Nino |
| 2018/0223912 | A1 | 8/2018 | Nino |
| 2018/0290274 | A1 | 10/2018 | Nino |

FOREIGN PATENT DOCUMENTS

| | | |
|---|---|---|
| WO | WO 2014/116414 A1 | 7/2014 |
| WO | WO 2014/116484 A1 | 7/2014 |
| WO | WO 2015/153376 A1 | 10/2015 |

OTHER PUBLICATIONS

International Patent Application No. PCT/US2016/055798; Int'l Written Opinion and Search Report; dated Dec. 29, 2016; 8 pages.
International Patent Application No. PCT/US2016/035712; Int'l Written Opinion and Search Report; dated Sep. 12, 2016; 13 pages.
International Patent Application No. PCT/US2016/054940; Int'l Preliminary Report on Patentability; dated Apr. 19, 2018; 10 pages.
"Sinusoidal clutch gives screwdriver precise torque", Product Engineering, Mcgraw-Hill Publication, New York, NY, US, (19730201), vol. 44, No. 2, ISSN 0032-9754, p. 14/15, XP002080526.
European Patent Application No. 16854340.3; Extended Search Report; dated Mar. 27, 2019; 8 pages.
International Patent Application No. PCT/US2016/055798; Int'l Preliminary Report on Patentability; dated Apr. 19, 2018; 8 pages.
International Patent Application No. PCT/US2017/014967; Int'l Preliminary Reporton Patentability; dated Mar. 14, 2019; 10 pages.
International Patent Application No. PCT/US2017/014970; Int'l Preliminary Reporton Patentability; dated Mar. 14, 2019; 9 pages.
International Search Report dated May 24, 2017, issued in International patent application PCT/US2017/014970 filed Jan. 25, 2017.
Written Opinion dated May 24, 2017, issued in International patent application PCT/US2017/014970 filed Jan. 25, 2017.
Office Action dated Aug. 10, 2020 for U.S. Appl. No. 16/337,909 (pp. 1-9).
Office Action dated Sep. 3, 2020 for U.S. Appl. No. 16/536,116 (pp. 1-9).
European Patent Office Invitation pursuant to Rule 62a(1) EPC dated Feb. 21, 2020, 2 pages.
European Patent Office Invitation pusuantto Rule 62a(1) EPC for App. No. EP17847106.6, dated Feb. 21, 2020, 2 pages.
Notice of Allowance dated Jan. 25, 2021 for U.S. Appl. No. 16/337,909 (pp. 1-9).
Zincland; Hypocycloid Gear Reduction, May 11, 2016. Retrieved from the Internet on Mar. 20, 2017. URL: <http://web.archive.org/web/20160511041614/http://www.zincland.com/hypocycloid/>.
Doctek; Hypocycloid How To Part 2—Some Experiments, Feb. 28, 2016. Retrieved from the Internet on Mar. 20, 2017. URL: <http://web.archive.Org/web/20160228057315/http://www.thingiverse.com/thing:81879> XP055470514.
Notice of Allowance issued for U.S. Appl. No. 16/536,116 dated Jun. 10, 2021.

* cited by examiner

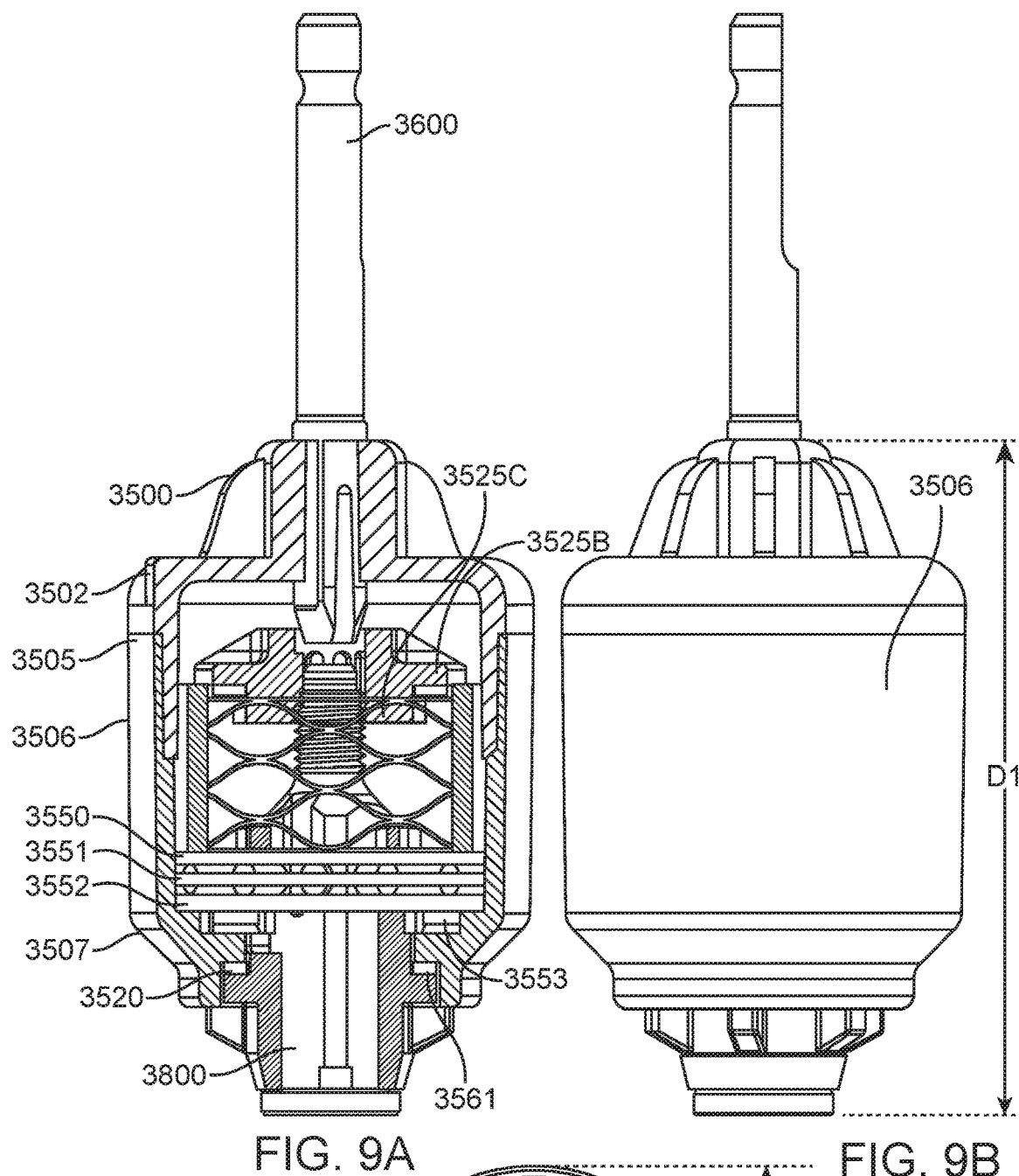
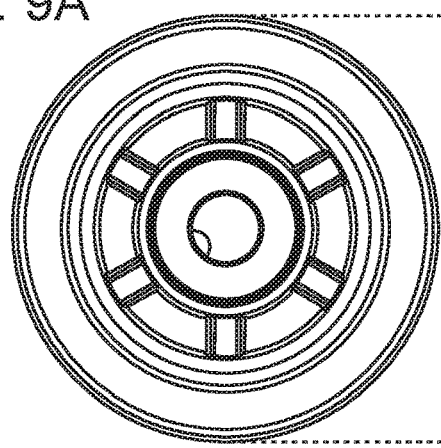
FIG. 9A   FIG. 9B   FIG. 9C

Testing Data of Device depicted in Figures 8, 9A-9D

GEARLESS IN-LINE TORQUE LIMITED DEVICE

CROSS-REFERENCE TO RELATED APPLICATIONS

This application is continuation of International Patent Application PCT/US2016/054940 filed Sep. 30, 2016, which claims priority to U.S. Provisional Patent Application No. 62/238,354, filed Oct. 7, 2015; and is a continuation of International Patent Application PCT/US2016/055798 filed Oct. 6, 2016, which claims priority to U.S. Provisional Patent Application No. 62/345,607 filed Jun. 3, 2016; U.S. Provisional Patent Application No. 62/238,419 filed Oct. 7, 2015; U.S. Provisional Patent Application No. 62/238,359 filed Oct. 7, 2015; is a continuation of International Patent Application PCT/US2016/035712 filed Jun. 3, 2016, which claims priority to U.S. Provisional Patent Application No. 62/238,419 filed Oct. 7, 2015 and to U.S. Provisional Patent Application No. 62/238,359 filed Oct. 7, 2015, the contents of which are incorporated here in their entirety.

BACKGROUND

1. Field

This disclosure relates to an in-line driver tool with a gearless torque-limiting assembly and, in particular, to a medical use torque-limiting driver that disengages at a predetermined torque limit.

2. General Background

Torque is a measure of force acting on an object that causes that object to rotate. In the case of a driver and a fastener, this measurement can be calculated mathematically in terms of the cross product of specific vectors:

$$\tau = r \times F$$

Where r is the vector representing the distance and direction from an axis of a fastener to a point where the force is applied and F is the force vector acting on the driver.

Torque has dimensions of force times distance and the SI unit of torque is the Newton meter (N-m). The joule, which is the SI unit for energy or work, is also defined as an N-m, but this unit is not used for torque. Since energy can be thought of as the result of force times distance, energy is always a scalar whereas torque is force cross-distance and so is a vector-valued quantity. Other non-SI units of torque include pound-force-feet, foot-pounds-force, ounce-force-inches, meter-kilograms-force, inch-ounces or inch-pounds.

Torque-limiting drivers are widely used throughout the medical industry. These torque-limiting drivers have a factory pre-set torque to ensure the accuracy and toughness required to meet a demanding surgical environment.

The medical industry has made use of both reusable and disposable torque-limiting drivers. In a surgical context, there is little room for error and these drivers must impart a precise amount of torque.

Reusable drivers require constant recalibration to ensure that the driver is imparting the precise amount of torque. Recalibration is a cumbersome task but must be done routinely. Such reusable devices also require sterilization.

Disposable drivers are an alternative to the reusable drivers. Once the driver has been used, it is discarded.

Disposable drivers are traditionally used for low torque applications. The standard torque values in these applications typically range from about 4 to about 20 inch-ounces. It has, however, been a challenge to develop a reliable disposable driver capable of imparting higher torques for larger applications.

Power tools are used for some applications in the medical industry. Such power tools can provide torque to a workpiece while also providing higher rotational rates than can be provided with manually driven tools. Torque-limiting systems can be utilized with medical power tools, either as an additional attachment provided in-line between the power tool and the workpiece or as internalized systems within the power tool itself. Reusable torque-limiting systems need to be sterilized between uses and typically must be serviced and recalibrated periodically to ensure performance within specifications. Disposable torque-limiting systems are an alternative to the reusable systems. Once the torque-limiting system has been used, it is discarded.

Disposable torque limiting devices which are inexpensive for use with power tools can fall out of specification with increased RPMs and as such fail to perform sufficiently. Bearings are typically used to reduce friction between moving parts.

Thus there is a need for disposable torque-limiting systems that can be utilized with medical power tools to limit applied torque at higher rotational speeds and remain in specification over a predetermined speed. The disclosure is directed to these and other important needs.

SUMMARY

This disclosure provides motor powered torque-limiting drivers comprising a cylindrical body having a fortified connector mount on one end and a nose cone at the other end, a drive shaft mounted in said connector mount, wherein the cylindrical body contains a gearless clutch assembly comprising a first clutch element affixed to the cylindrical body, a second clutch element engaged with a shaft for rotation together with the shaft, one or more bearing elements disposed between the first clutch element and the second clutch element, and a compressive element configured to apply force against one of the first clutch element and second clutch element in the direction of the other clutch element, which is held fixed in relation to the nose cone. The first clutch element and second clutch element can exert compressive force, shearing force, or both on the one or more bearing elements, such that the first clutch element and second clutch element engage for rotation together when a motor applies rotational force to the drive shaft. The first clutch element and second clutch element can disengage when a predetermined torque limit is exceeded.

This disclosure provides motor powered torque-limiting drivers comprising a cylindrical body having a fortified connector mount affixed at a proximal end and a nose cone partially inserted into a distal end of the cylindrical body, the nose cone having a keyed external profile at the end inserted into the cylindrical body and a drive socket within an axial bore of the nose cone, a drive shaft mounted in said connector mount, wherein the cylindrical body contains an upper thrust washer having a keyed internal profile that is mated to the keyed external profile of the nose cone, a lower thrust washer affixed to the cylindrical body, a bearing element disposed between the upper thrust washer and lower thrust washer, a connector having a tip a drive connection and a threading, the connector being engaged within the drive socket of the nose cone, a nut having internal features to engage with the threading of the connector, and a compression element between the upper thrust washer and nut, wherein the compression element is configured to apply a force across the upper thrust washer and the lower thrust washer to compress the bearing element. The bearing element can be compressed such that the upper thrust washer and lower thrust washer engage for relative rotation when a motor applies rotational force to the drive shaft and the upper thrust washer and lower thrust washer can disengage when a predetermined torque limit is exceeded.

This disclosure provides motor powered torque-limiting drivers comprising a cylindrical body having a fortified connector mount on one end and a nose cone at the other end, a drive shaft mounted in said connector mount, wherein the cylindrical body contains an upper cylindrical shank having a first bearing shearing element (181) around an axial bore, a lower cylindrical shank having a second bearing shearing element (182) around a drive socket (9), a plurality of bearing elements disposed between the first bearing shearing element and the second bearing shearing element, a shaft assembly (50) having a drive connection (16) and a threading (18) engaged within the drive socket of the lower cylindrical shank, the shaft extending through the axial bore, a nut 25 having internal features to engage with the threading, and a spring (22) between the upper cylindrical shank and nut, wherein the spring is configured to apply a force across the upper cylindrical shank and the lower cylindrical shank, and wherein the spring is connected via the threading to the nut. The plurality of bearing elements can be subjected to compression, shearing force, or both such that the upper cylindrical shank and lower cylindrical shank engage for relative rotation when a motor applies rotational force to the drive shaft. The upper cylindrical shank and the lower cylindrical shank can disengage when a predetermined torque limit is exceeded.

This disclosure provides gearless clutch assemblies comprising a first clutch element, a second clutch element, one or more bearing elements disposed between the first clutch element and the second clutch element, and a compressive element configured to apply force against one of the first clutch element and second clutch element in the direction of the other clutch element. The first clutch element and second clutch element can exert compressive force, shearing force, or both on the one or more bearing elements, such that the first clutch element and second clutch element engage for rotation together. The first clutch element and second clutch element can disengage when a predetermined torque limit is exceeded.

This disclosure provides torque limiting methods, the methods comprising placing an upper thrust washer having a keyed internal profile that is mated to the keyed external profile of a nose cone in a substantially hollow body, affixing a lower thrust washer in the body, placing a bearing element between the upper thrust washer and lower thrust washer, affixing the thrust washers and bearing element into a drive train via a connector having a tip, a drive connection, and a threading, the connector being engaged within a drive socket of the nose cone, a nut having internal features to engage with the threading of the connector, and a compression element between the upper thrust washer and nut, wherein the compression element is configured to apply a force across the upper thrust washer and the lower thrust washer to compress the bearing element, wherein the bearing element is compressed such that the upper thrust washer and lower thrust washer engage for relative rotation when a motor applies rotational force to the drive shaft; and, wherein the upper thrust washer and lower thrust washer disengage when a predetermined torque limit is exceeded.

DRAWINGS

The above-mentioned features of the present disclosure will become more apparent with reference to the following description taken in conjunction with the accompanying drawings wherein like reference numerals denote like elements. In addition, the drawings are not necessarily drawn to scale.

Figure 3A:
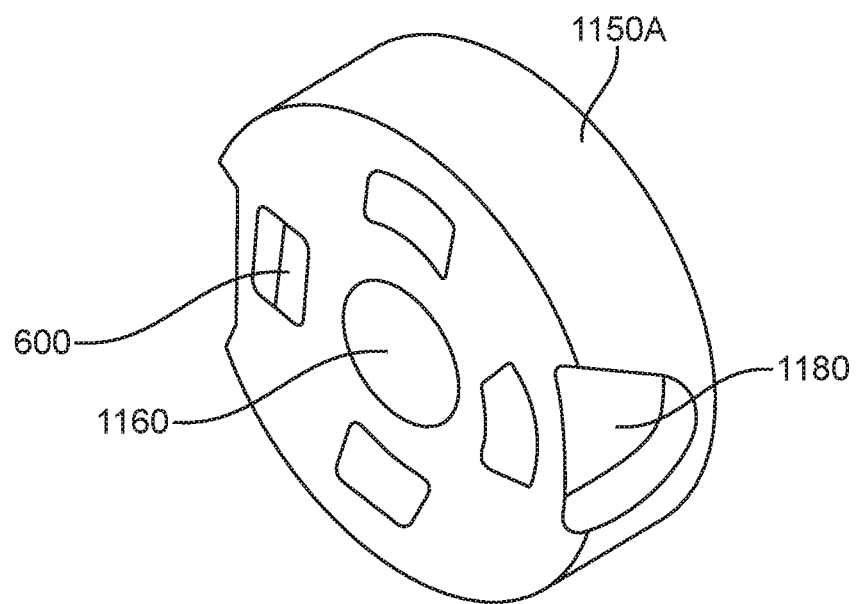
Figure 3B:
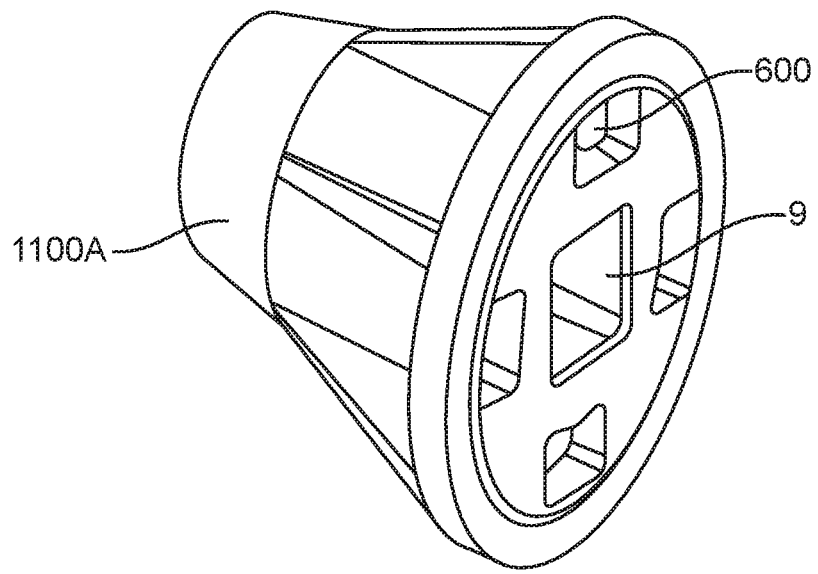
Figure 3C:
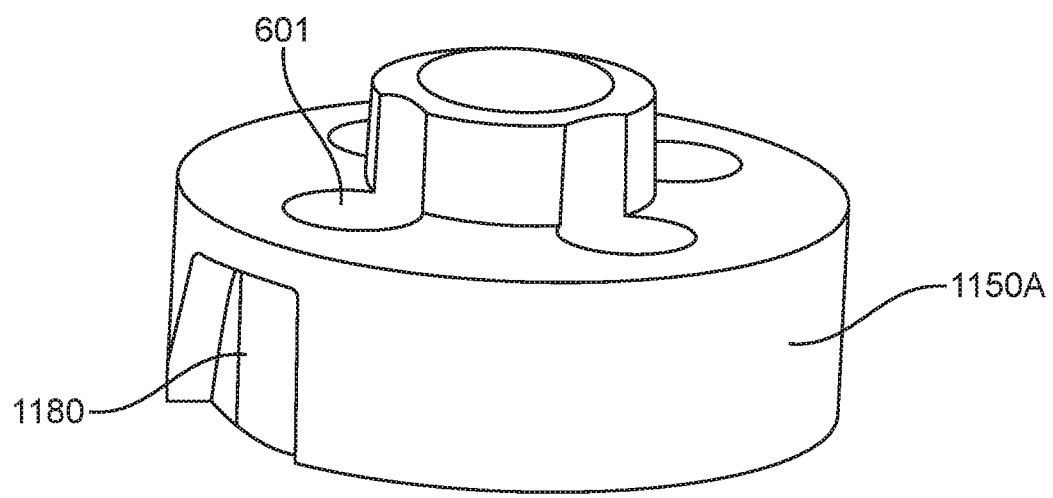
Figure 4A:
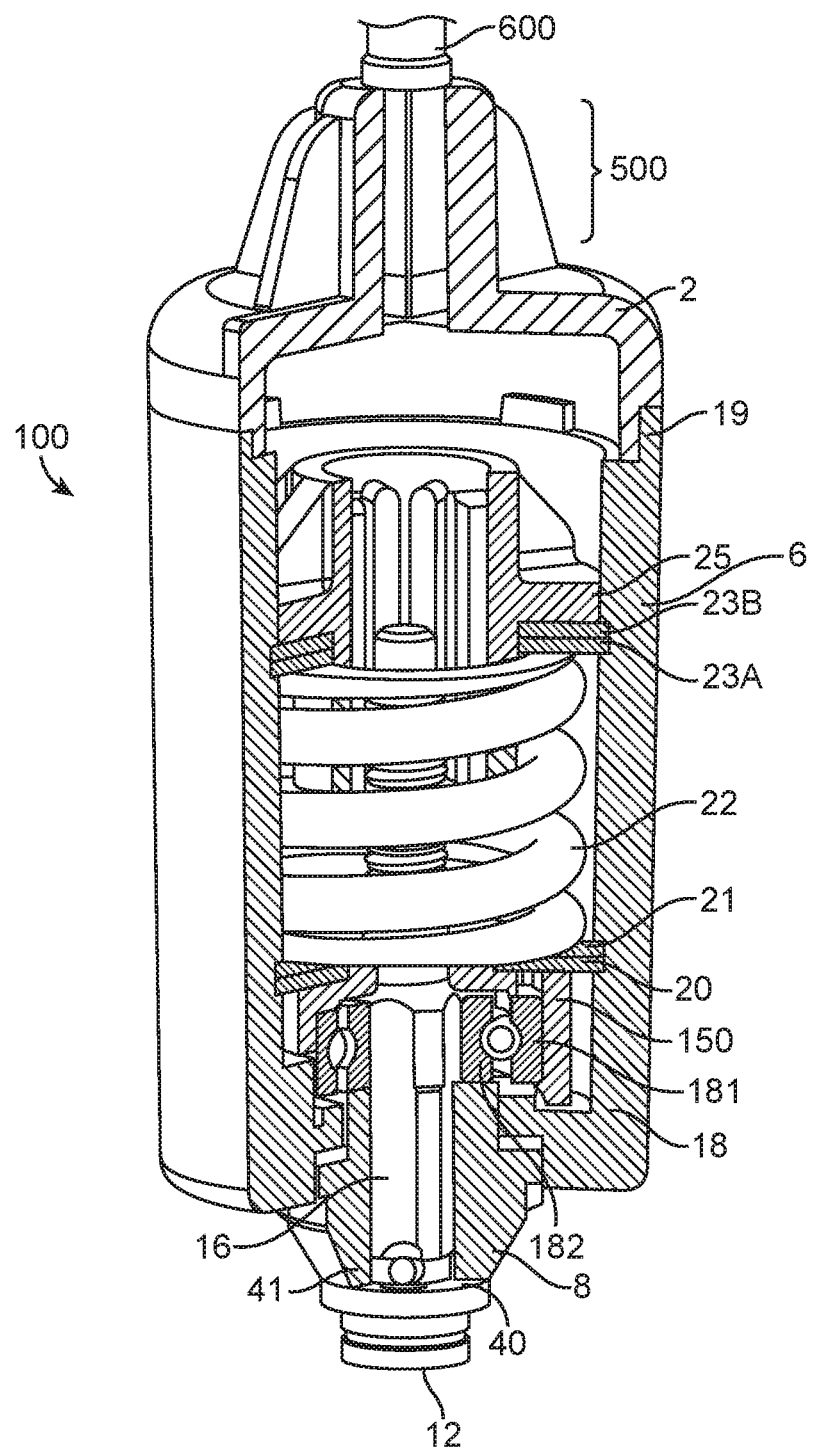
Figure 4B:
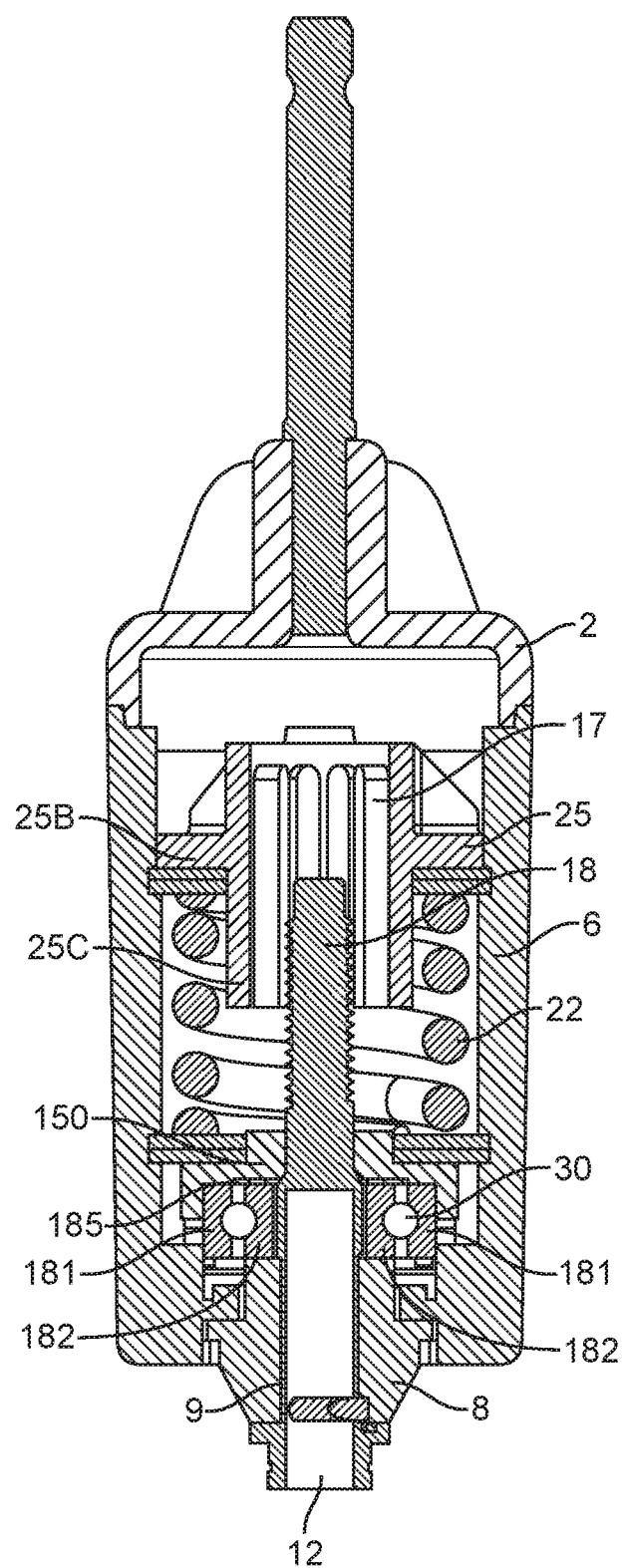
Figure 5:
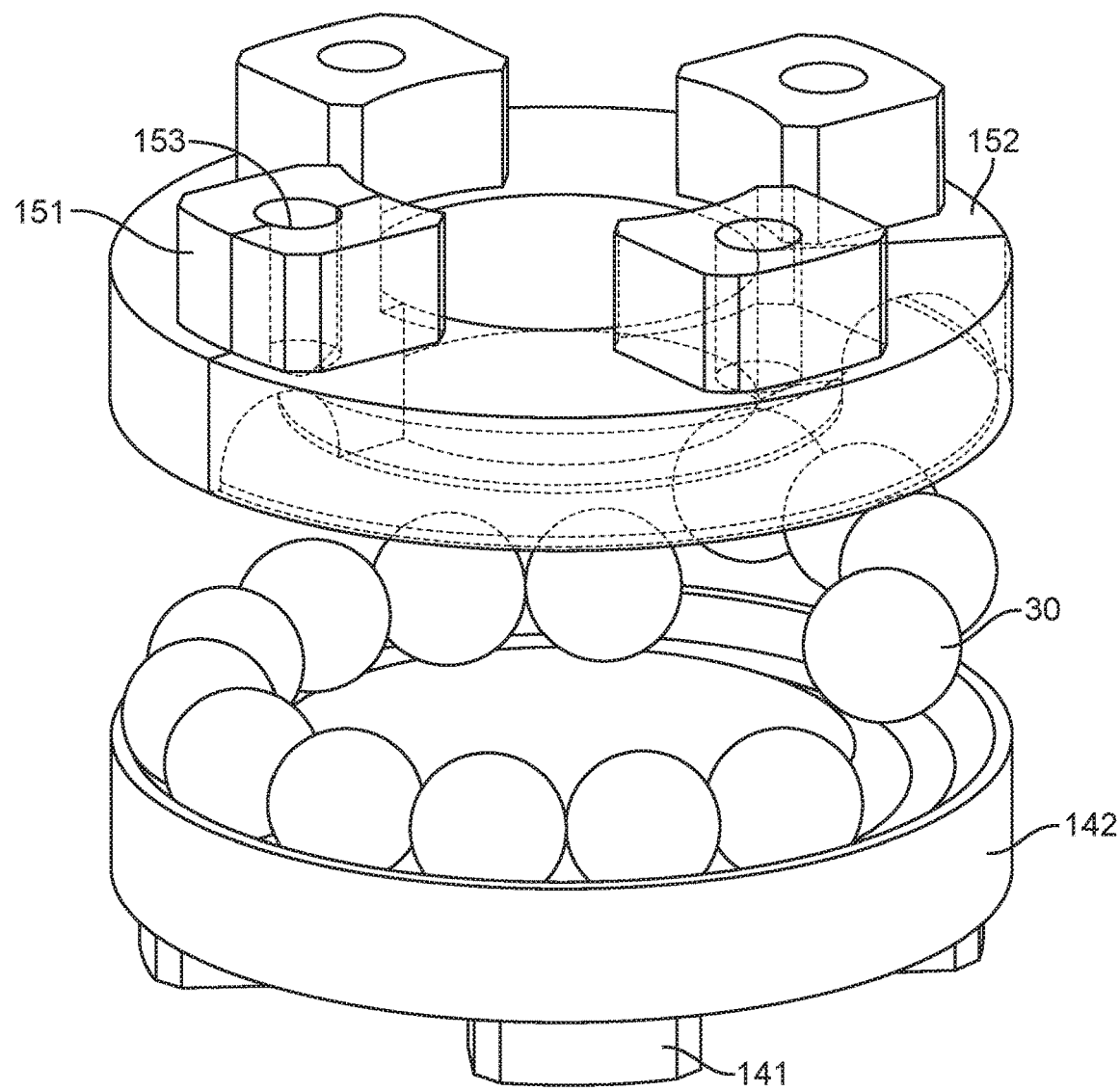
Figure 6:
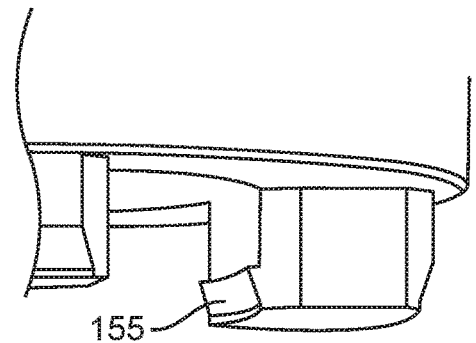
Figure 7A:
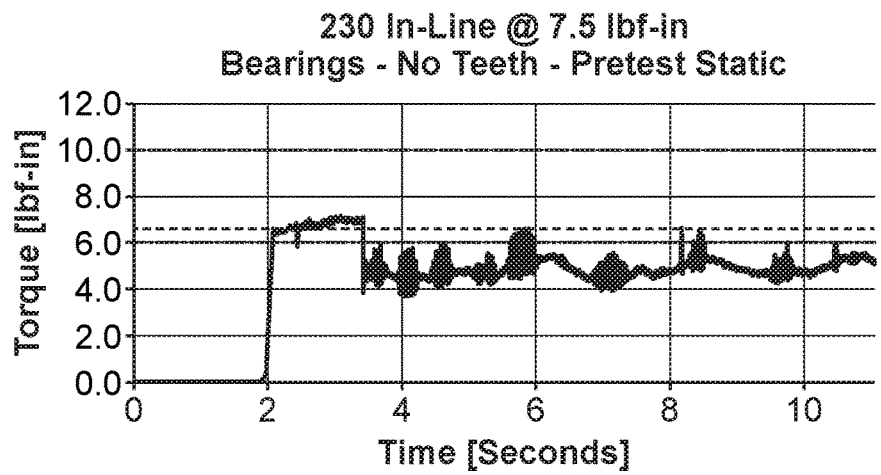
Figure 7B:
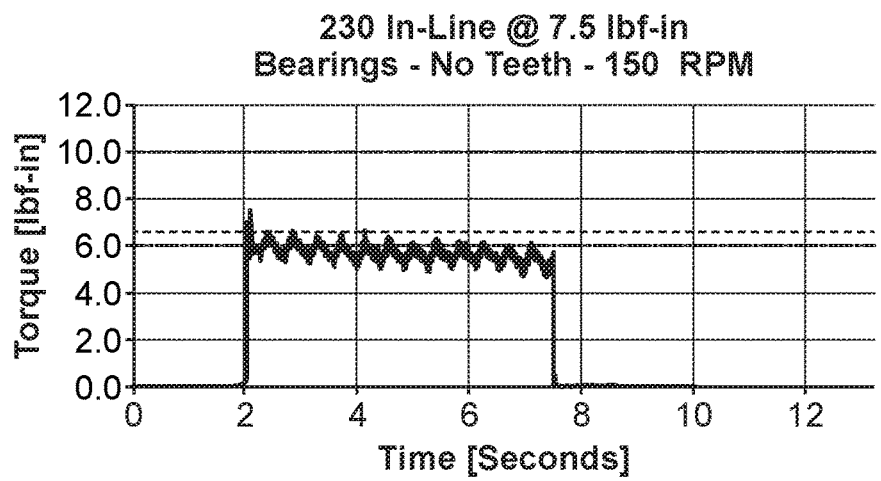
Figure 7C:
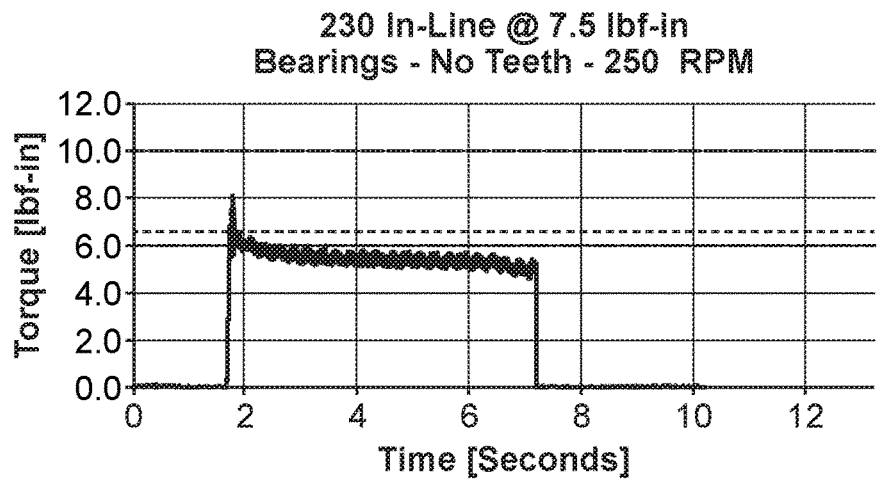
Figure 7D:
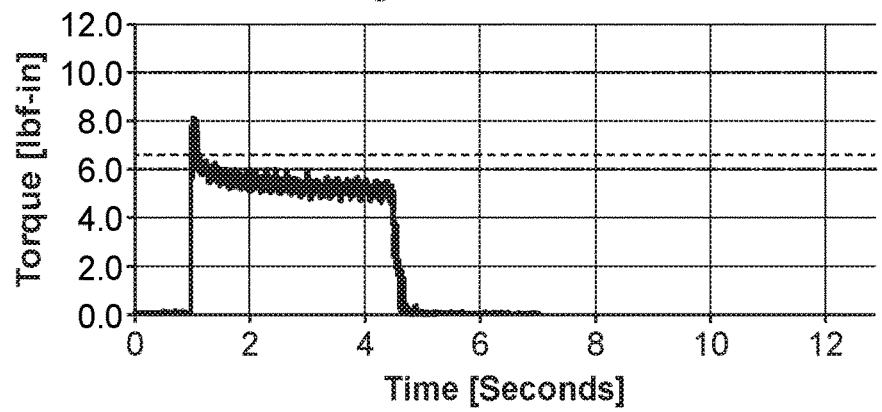
Figure 7E:
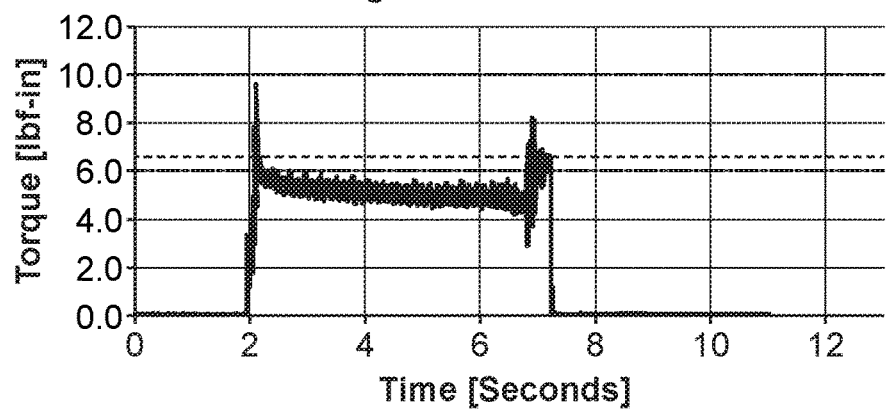
Figure 7F:
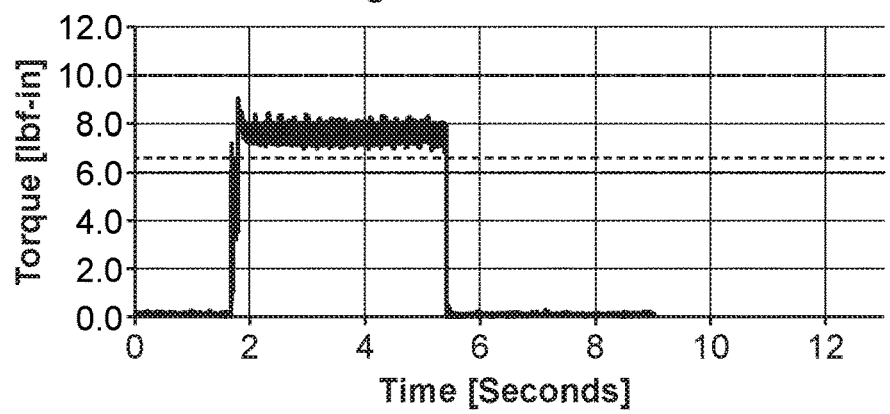
Figure 7G:
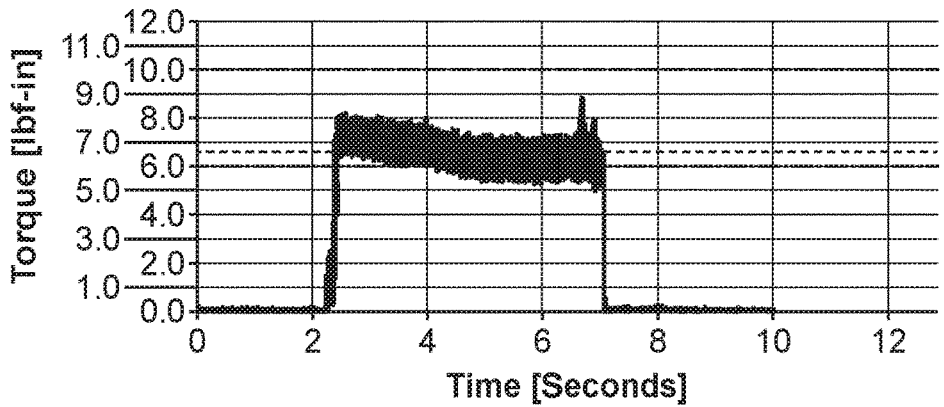
Figure 7H:
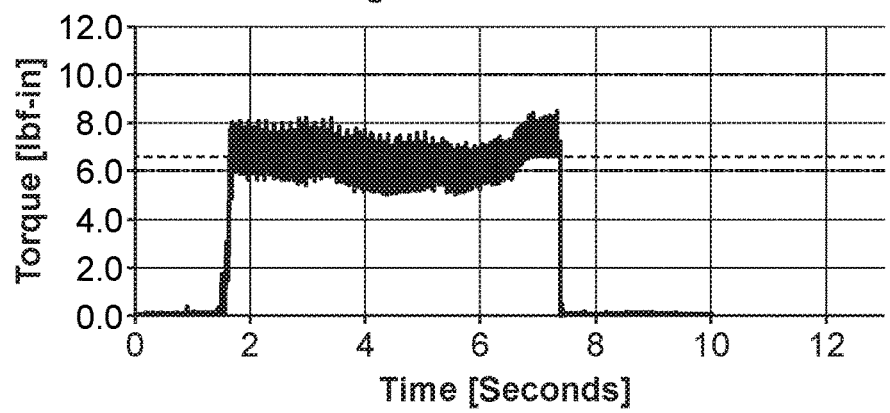
Figure 7I:
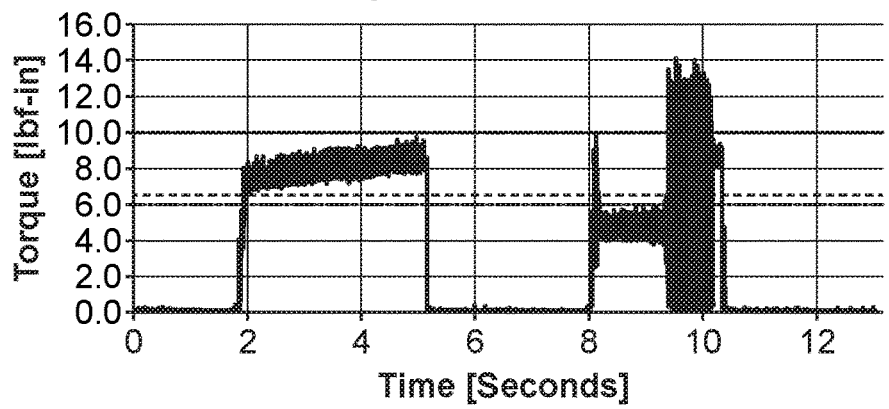

FIGS. 3A, 3B, and 3C show some aspects of in-line torque-limiting devices of the present disclosure;

FIG. 4A shows a partial cutaway view of some aspects of an implementation of an in-line torque limiting device;

FIG. 4B shows a cutaway view of some aspects of an implementation of an in-line torque limiting device shown in FIG. 4A;

FIG. 5 shows an exploded assembly perspective view of some aspects of an implementation of a bearing assembly suitable for use in implementations of in-line torque limiting devices of the present disclosure;

FIG. 6 shows a perspective view of some aspects of implementations of a bearing assembly;

FIGS. 7A-7I are test data at various RPM's of the implementations in FIGS. 4A-6

Figure 8:
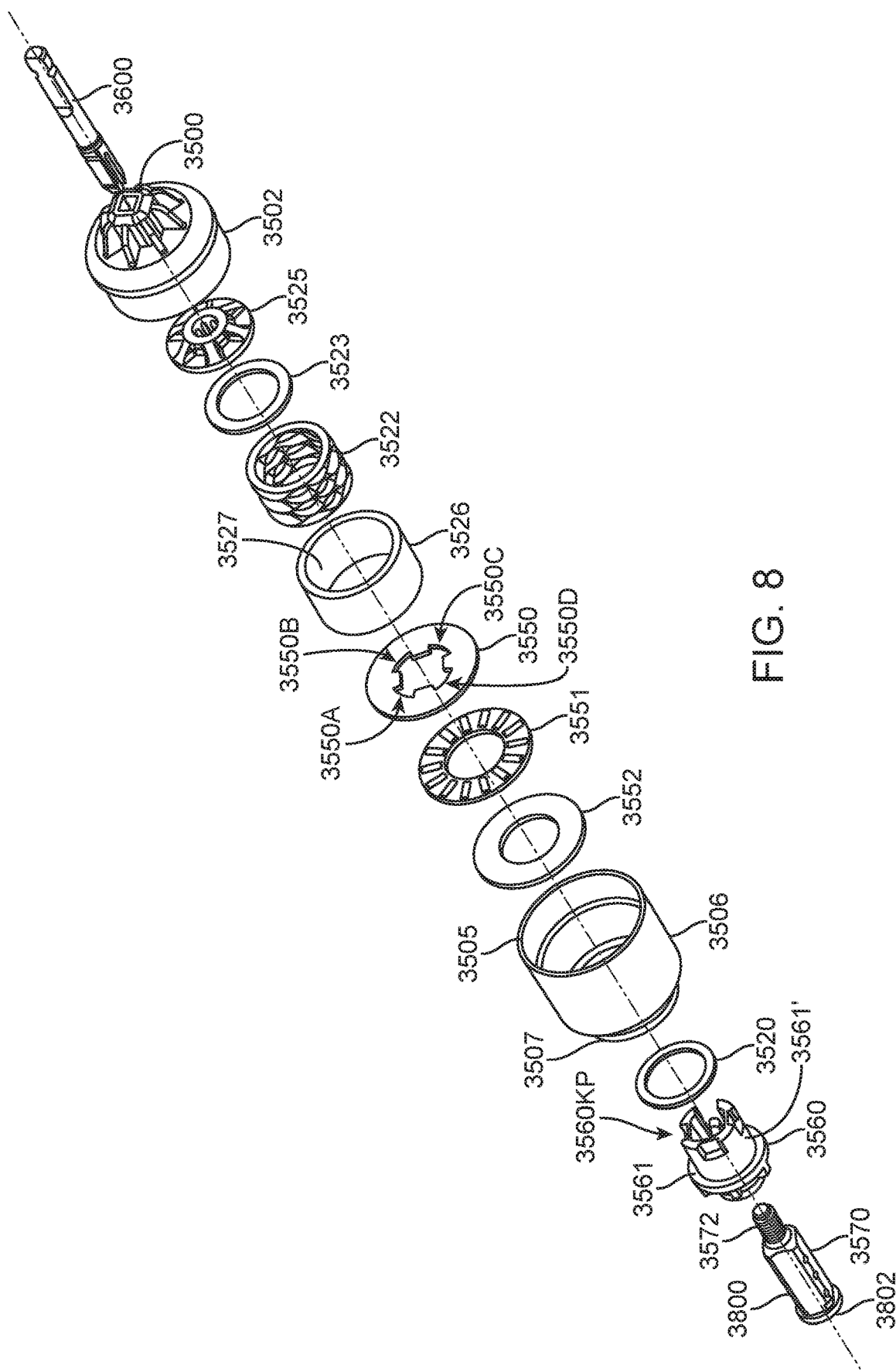
Figure 9D:
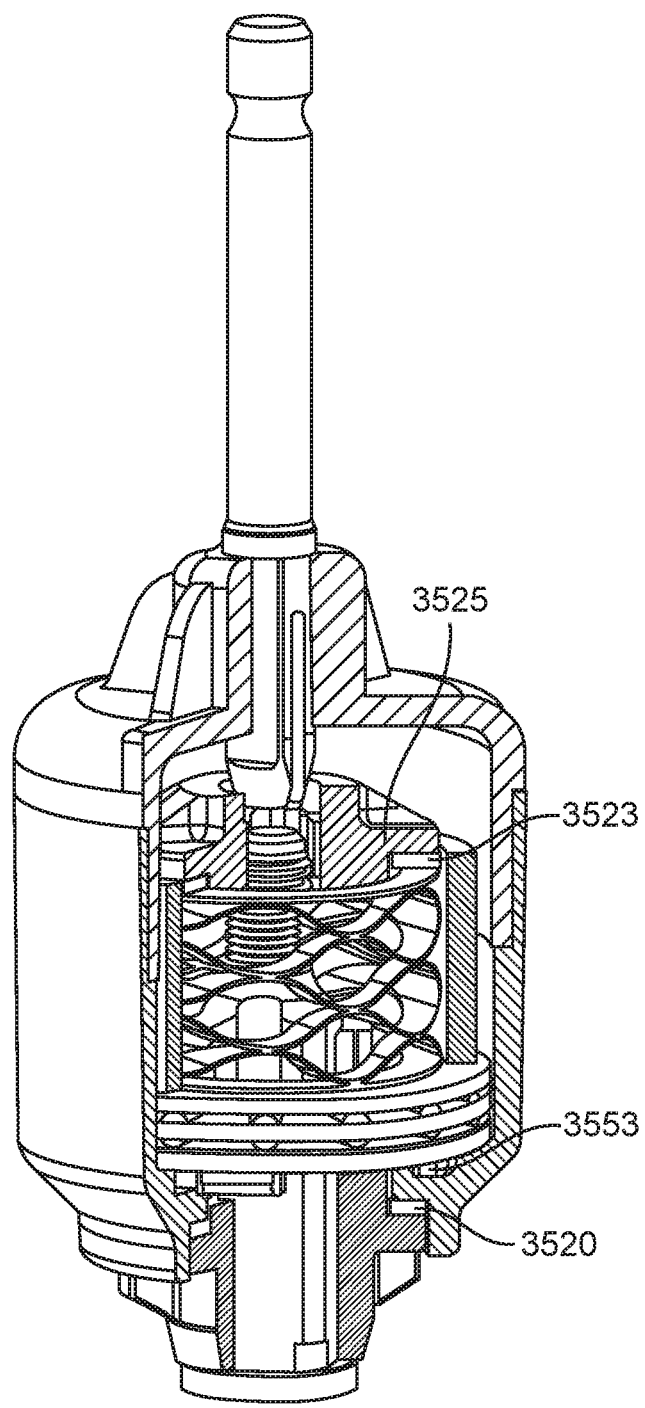
Figure 10A:
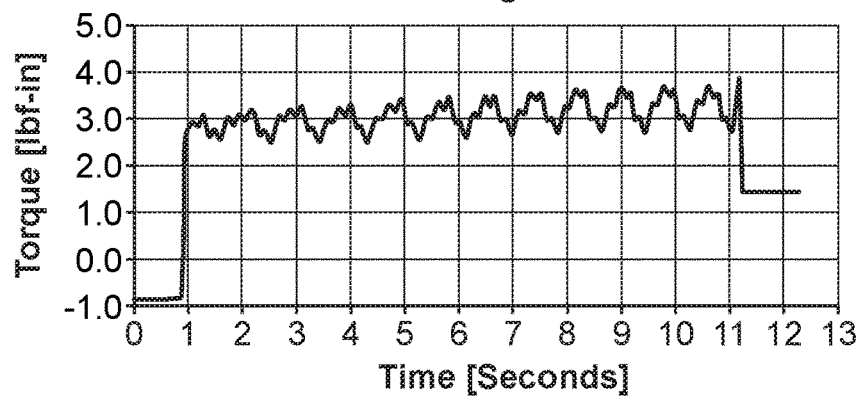
Figure 10B:
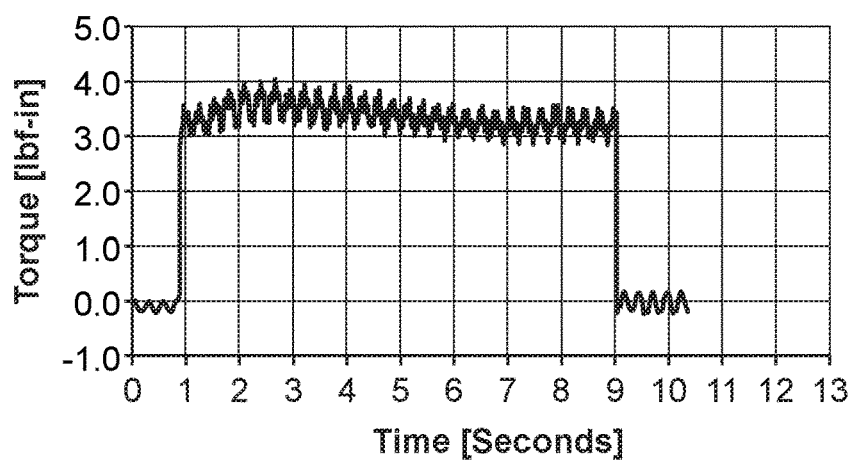
Figure 10C:
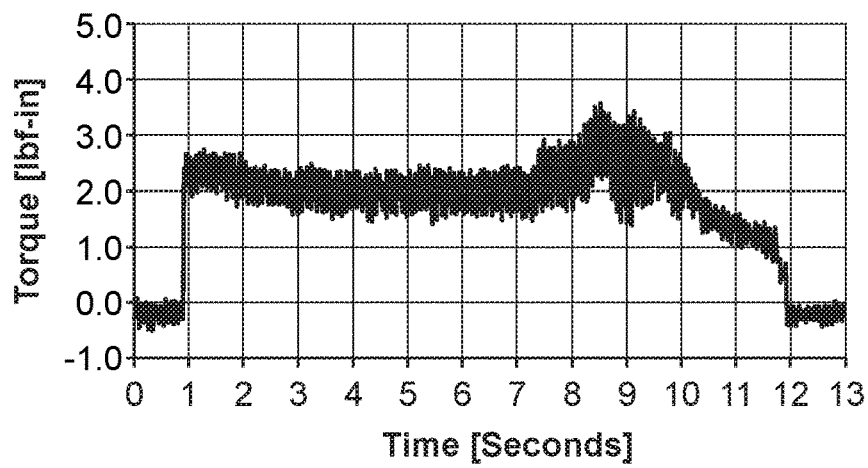
Figure 10D:
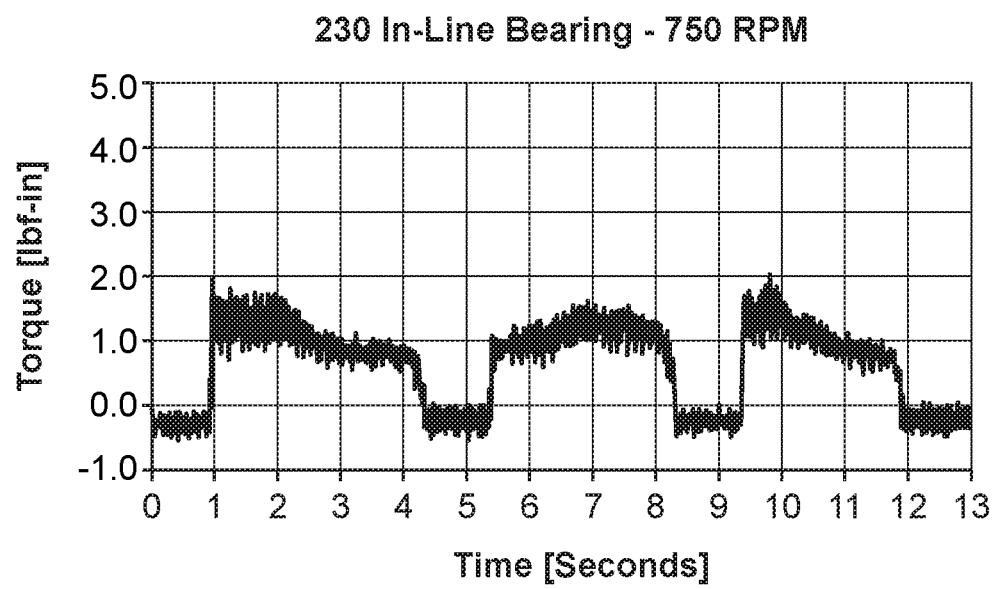
Figure 10E:
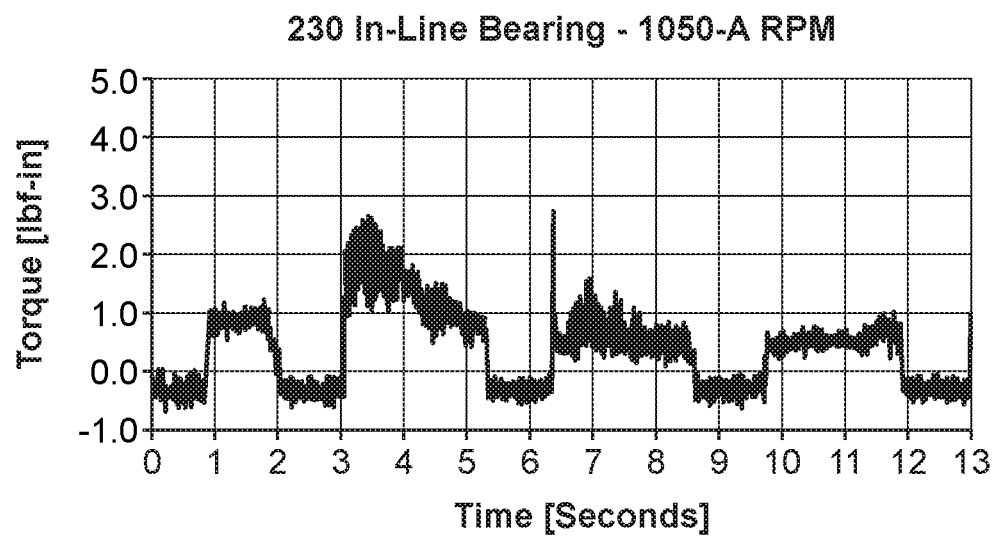

FIG. 8 shows an exploded assembly perspective view of a powered in-line torque limiting device;

FIGS. 9A, 9B, 9C, and 9D show cutaway, side, top, and partial cutaway views of some aspects of an implementation of a powered in-line torque limiting device of the present disclosure; and, FIGS. 10A-10E show testing data of implementations of a powered in-line torque limiting devices in FIGS. 8-9D.

While the specification concludes with claims defining the features of the present disclosure that are regarded as novel, it is believed that the present disclosure's teachings will be better understood from a consideration of the following description in conjunction with the figures in which like reference numerals are carried forward. All descriptions and callouts in the Figures are hereby incorporated by this reference as if fully set forth herein. The failure to number an element in a figure is not intended to waive any rights, and unnumbered references may also be identified by alpha characters in the figures.

FURTHER DESCRIPTION

Figure 1:
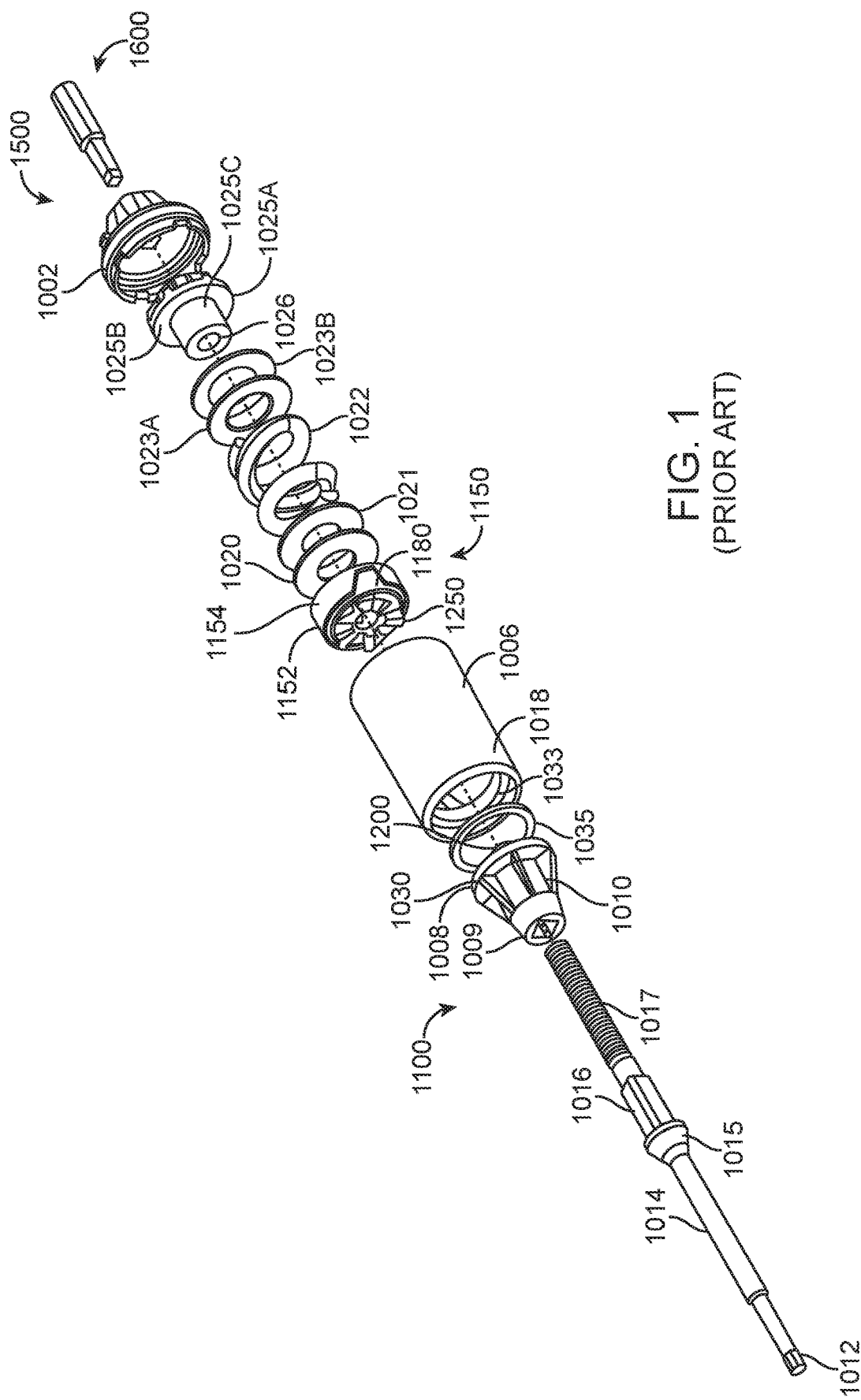
FIG. 1 shows an exploded assembly perspective view of some aspects of a prior art in-line torque limiting device.
Figure 2:
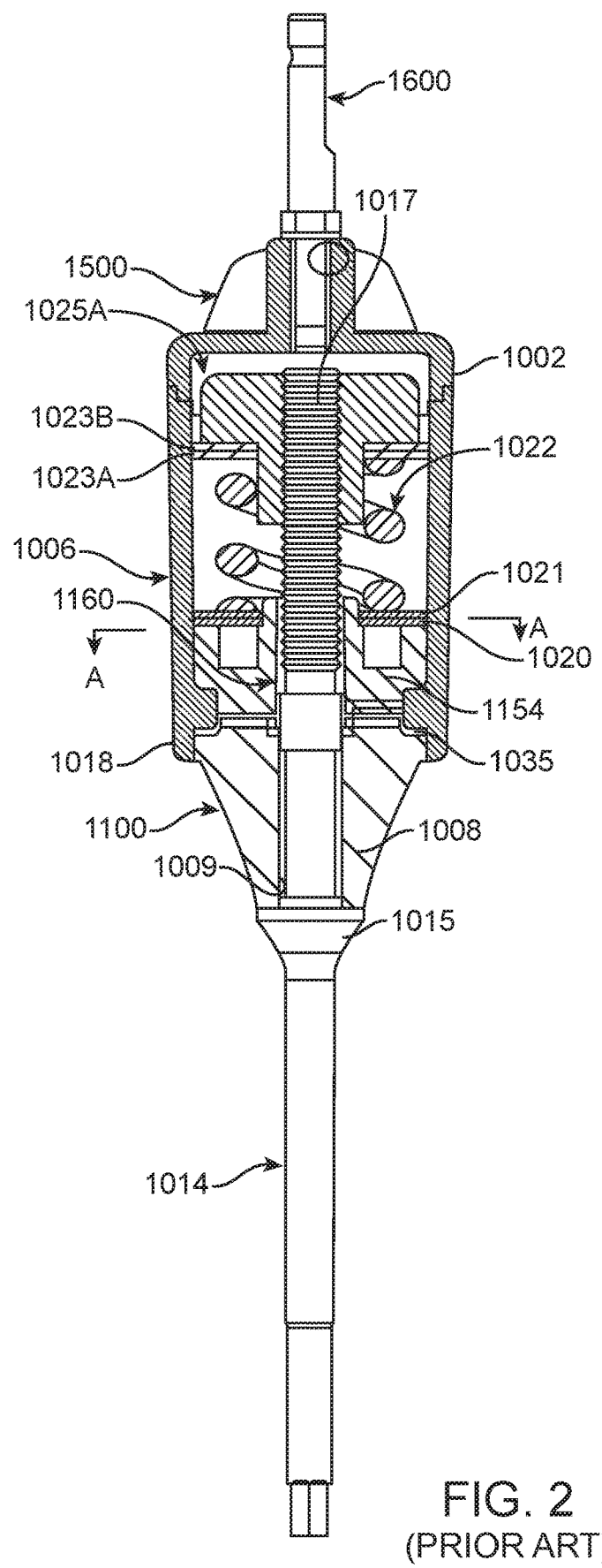
FIG. 2 shows a cutaway front view of some aspects of a prior art in-line torque limiting device.

An implementation of a prior art powered in-line torque limiting driver is depicted in FIGS. 1 and 2, and is further disclosed in International Patent Application Nos. PCT/US2015/023147 and PCT/US2014/010550, which are incorporated by reference as if fully set forth herein. The driver may have a generally cylindrical body with a cup shaped drive cap 1002 or other structure to facilitate use by a user. For example, the drive cap is affixed to a generally hollow cylindrical body 1006. Cylindrical distal end 1018 terminates cylindrical body 1006 toward tip 1012 of tool shaft 1014. Cap 1002 is mated to the cylindrical body at the proximal end 1019 of the cylindrical body the cap 1002 may be snap-fitted to cylindrical body 1006, or may be welded, adhered, or attached by any equivalent thereof. A connector mount 1500 is shown formed on the cap. The connector mount 1500 provides a fixation of a drive shaft 1600 for a powered in-line torque limited driver. The power source is preferably an electric motor. The motor may apply at least one of force and rotational speed in excess of a human operator. In use, the drive shaft imparts rotational force to the connector mount 1500 which is fixed to the cap 1002 and body 1006 thereby rotating engaged crown gears within the body and rotating the nose cone 1008 and attached tool 1012.

At cylindrical distal end 1018, lower shank 100 has an annularly tapering body and nose cone 1008 along its length. Lower shank 1100 may have a plurality of support flanges 1010 that add strength while saving material. At one end, lower shank 1100 tapers to drive socket 1009 at the end of the nose cone 1008 molded to engage drive connection 1016 of tool shaft 1014. An exemplary implementation shows, at least in part, shaft 1014 provided, at one end, with workpiece-engaging tip 1012, adapted for engagement with an associated workpiece, such as a fastener or the like. Workpiece-engaging tip 1012 is shown to be a hex type wrench but could be a screwdriver, wrench, socket wrench, or any other tool arrangement. At an opposite end, lower shank 1100 has a plurality of teeth 1200 arranged in a crown gear formation, with circumferential rim 1030 extending radially outward and an internal axial bore to accommodate at least a portion of shaft 1014 extending there through.

Inside cylindrical body 1006 a clutch assembly is disposed. The clutch assembly 1240 includes upper shank 1150 for forcibly engaging lower shank 1100. Upper shank 1150 has a bottom face that has a plurality of teeth 1250 arranged in a crown gear formation and circumferential rim 1152 extending radially outward. Upper shank 1150 includes an annular outer cylindrical shank wall 1154 and an axial bore 1160. Upper shank 1150 includes at least one recess 180 on a side of the annular outer cylindrical shank wall 1154. Recess 1180 is provided as a cylindrical cut, relief or recess into the side of the outer shank and maybe provided as a square or rectangular cut or the cut may have a slanted side or sides relative to the axis of upper shank 1150.

In assembly, drive connection 1016 of tool shaft 1014 is received into drive socket 9 of lower shank 100. In some instance a square drive socket 1009 is preferred and the drive connection is a corresponding shape. Washer 1035 maybe provided between the bearing surface of circumferential rim 1032 of lower shank 1100 and a circumferential flange 1033 extending radially inward within the hollow of cylindrical body 1006. Washer 1035 may be of a polymer or other material having low coefficient of friction. Alternatively, circumferential rim 32 of lower shank 100 may be provided flush against circumferential flange 1033 of cylindrical body 1006. The opposite side of circumferential flange 33 receives circumferential rim 1152 of upper shank 1150, allowing teeth 1200 of lower shank 1100 to engage teeth 1250 of upper shank 1150 when a torque is applied.

Integrally formed within cylindrical body 1006, protrusion 1185 (not shown) mates with recess 1180 of upper shank 1150. Protrusion 1185 extends inward in a radial fashion and has a length along the axis of cylindrical body 1006 for relative moveable engagement within recess 1180. This engagement provides a locking mechanism of shaft 1014 relative to the handle via upper shank 1150 when pressure is applied across lower shank 1100 and upper shank 1150. Recess 1180 is provided circumferentially wider than protrusion 1185 for allowing cylindrical body 1006 and the cap 1002 to rotate in reverse a predetermined distance from a locked position without subsequent reverse rotation of workpiece-engaging tip 1012. Thus, at least one recess 1180 and at least one protrusion 1185 lock the body in one direction providing the necessary torque to drive a fastener and allow for a predetermined amount of reverse rotation before unscrewing the fastener.

Force is applied across lower shank 1100 and upper shank 1150 via spring 1022 within cylindrical body 1006. Inside cylindrical body 1006, washer one 1020 and washer two 1021 are provided between upper shank 1150 and spring 1022. The washers transfer pressure from spring 1022 over the top face of upper shank 1150. At an end of spring 1022 opposite upper shank 150, washer three 1023 and nut 1025A hold spring 1022 in a relatively compressed state. Washer 1023 may be provided between nut 1025A and spring 1022 to facilitate relative rotation of nut 1025A and spring 1022. Nut 1025A is formed of material softer than shaft 1014, nut 1025A has an unobstructed open center 1026 with a diameter smaller than the diameter of shaft 1014 and a smooth surface malleable enough to be deformed by the rotational insertion to said open center 1026 of the threading 1017 at an end of shaft 1014. A cup washer may replace nut 1025A.

An enhanced nut 1025A may provide an upper shoulder portion 1025B having a diameter larger than the inner diameter of spring 1022 and a lower neck portion 1025C having outer diameter substantially equal to an inner diameter of spring 1022. The lower neck portion 1025C of nut 1025A may extend axially through at least a portion of spring 1022. At least one of the upper shoulder portion 1025B and the lower neck portion 1025C of nut 1025 may maintain relative axial alignment between nut Closing the handle and device is a cap 1002. The cap supports a mount 1500, which may be fortified as detailed in International Patent Application No. PCT/US2014/011719, incorporated by reference herein in its entirety. Those of ordinary skill in the art will recognize that a variety of mounts may be utilized to support a drive shaft 1600 and the illustration of a fortified mount is not a limitation.

The gearless clutch systems of the present disclosure, depicted in FIGS. 3-8D are able to at least one of withstand, buffer, and sink the heat from the friction caused from high RPM uses and provide for more consistent torque limits at high RPMs. The gearless clutch systems of the present disclosure are implemented in in-line torque limiters that function similarly to the prior art systems depicted in FIGS. 1-2, except that the crown gear systems are replaced with gearless bearing systems. The bearing systems are subjected to compression forces, shearing forces, or both to resist relative rotation across their top and bottom surfaces, and the resistance is overcome at predetermined torque limits to provide torque-limiting functionality.

Aspects of an implementation of an in-line torque limiting device of the present disclosure are shown in FIGS. 4A and 4B. Powered in-line torque limiting driver 100 may have a generally cylindrical body with a cup shaped drive cap 2 or other structure to facilitate use by a user. For example, the drive cap is affixed to a generally hollow cylindrical body 6. Cylindrical distal end 18 terminates cylindrical body 6 toward tip connection 12 of shaft assembly 50. Cap 2 is mated to the cylindrical body at the proximal end 19 of the cylindrical body the cap 2 may be snap-fitted to cylindrical body 6, or may be welded, adhered, or attached by any equivalent thereof. A connector mount 500 is shown formed on the cap. The connector mount 500 provides a fixation of a drive shaft 600 for a powered in-line torque limited driver. The power source is preferably an electric motor. The motor may apply at least one of force and rotational speed in excess of a human operator. In use, the drive shaft imparts rotational force to the connector mount 500 which is fixed to the cap 2 and body 6 thereby rotating the nose cone 8 and tip connection 12.

Shaft assembly 16 includes a threaded portion 18 at one end and tip connection 12 at the opposite end. Tip connection 12 is configured to receive a workpiece engaging tip. Suitable configurations for tip connection 12 and workpiece engaging tips are disclosed in U.S. Patent Publication No. US2013/0226192 A1, which is incorporated by reference herein in its entirety. Shaft assembly 50 further includes a drive connection profile 16 that interfaces within a drive socket 9 within nose cone 8.

In assembly, the threaded portion 18 of shaft assembly 50 is threaded into nut 25 via the thread rests 17 within the nut 25. The threading of the shaft assembly cuts threads into the plurality of thread rests within the axial bore of the nut 25. Nut 25 is formed of a material softer than the threaded portion 18 of the shaft assembly 50. In alternative implementations, nut 25 could be a threaded metal nut. Nut 25 may provide an upper shoulder portion 25B having a diameter larger than the inner diameter of spring 22 and a lower neck portion 25C having outer diameter substantially equal to an inner diameter of spring 22. Washers 23A and 23B rest on shoulder portion 25B of nut 25. Lower neck portion 25C of nut 25 may extend axially through at least a portion of spring 22.

Ball bearings 30 are subjected to a shearing and compression forces between an upper shank 150 with a first bearing shearing element 181 and second bearing shearing element 182 that is connected to the top of nose cone 8. Elements 181 and 182 are rings with grooves that interface with ball bearings 30; element 181 has a groove along its internal axial bore while element 182 has a groove along the outer circumference of the ring. Element 182 is fixed in relative vertical position via the connection to nose cone 8, which is held against the bottom end 18 of body 6 via the shaft assembly collar 40 pushing against the distal end 41 of the nose cone 8. A gap 185 is provided between the top of element 182 and the adjacent surface of upper shank 150, such that the parts do not rub against each other when the bearings disengage. Element 181 is forced downwards by the force of spring 22 against the top of upper shank 150 through the washers 20 and 21. Elements 181 and 182, by being sheared against each other exert force on the ball bearing elements 30. The compression provided by spring 22 can be calibrated by the tightening of nut 25 onto threading 18 in order to apply the necessary shear force across the bearing elements to provide the predetermined torque limit. When the predetermined torque limit is reached, the ball bearing elements begin to roll, and element 182 begins to rotate with nose cone 8 relative to upper shank 150 and element 181 which are held fixed to the body 6 via an internal engagement (not shown). The internal engagement may be similar to the engagement within cylindrical body 1006 of protrusion 1185 mating with recess 1180 of upper shank 1150, as described above with reference to FIGS. 1 and 2 and further described in International Patent Application No. PCT/US2015/023147.

Upper shank 115 can be affixed with first bearing shearing element 181 with a system of mating features. In some implementations a plurality of dog catches 600 can be provided in the bottom face of an implementation of an upper shank 1150A as shown in FIG. 3A. These dog catches receive corresponding dog latches 151 in element 181. The dog latches can be provided with threaded holes for attachment with fasteners that are inserted through holes 601 in the opposing face of upper shank 1150A, as seen in FIG. 3C.

The second bearing shearing element 182 can be connected to the top of an implementation of nose cone 8 via similar dog catches and latches, such catches 600 can be seen in FIG. 3B.

In other implementations of the present disclosure, bearing guides 142 and 152, as shown in FIGS. 5 and 6 are used in conjunction with the upper shank 1150A and lower shank 1100A depicted in FIGS. 3A-3C. In these implementations little or no shear force is present as in the implementations described in FIGS. 4A and 4B; instead, compressive force is applied to the ball bearings to resist their rotation. Lower shank 1100A and upper shank 1150A interface with their corresponding bearing guides 142 and 152. Bearing guides 142 and 152 act to retain bearings 30, as shown in FIG. 5. A minimal amount of silicone lubricant can be provided in the grooves retaining the ball bearings. The bearing guides are connected to the shanks via the mating features shown in FIGS. 3A-3C, wherein dog latches and dog catches that interface together. Bearing guides 142 and 152 may be connected to the lower and upper shanks via threaded connections 143/153 within dog latches 141/151. Alternatively, the dog latches 141/151 may be barbed with barbs 155 such that the bearing guides 142/152 may be press-fit into the lower and upper shanks. Once the upper and lower shanks are assembled together with the bearing guides 142 and 152, they can be incorporated into the implementations shown in FIGS. 1 and 2 to replace upper shank 1150 and lower shank 1100.

Washers 20 and 21 transfer pressure from spring 22 onto the top of the upper shank 150. As the nut is tightened onto the shaft assembly 50, spring 22 is compressed, which compresses the bearings 30 within the channel formed between bearing guides 142/152. The compression of spring 22 is calibrated through the nut tightening to the desired level to achieve a predetermined torque limit. The nose cone 8 will turn with the body 6 until the predetermined torque limit is reached, at which point the bearing guides 142/152 will begin to turn past each other as bearings 30 roll and allow the relative movement.

Testing data from an implementation shown in FIGS. 4A-6 is shown in FIGS. 7A-7I. A predetermined torque limit of approximately 7.5 pound-inches was selected via tightening of nut 25.

In other implementations of in-line torque limiting devices of the present disclosure, as depicted in some aspects in FIGS. 8 and 9A-9E, the bearing clutch can comprise a roller bearing 3551 that is compressed between two thrust washers 3550 and 3552. An external mating shaft 3600 interfaces with connector mount 3500 in cap 3502. Cap 3502 is affixed to a generally hollow cylindrical body 3506 at proximal end 3505. A compression nut 3525 is connected to an internal shaft and mating connector 3570 via one threaded end of the connector 3570 which threadably connects within an internal axial bore of nut 3525. One or more washers 3523 can be disposed between nut 3525 and a compression element 3522, which is contained within a containment sleeve 3526. The containment sleeve 3526 has an interior annular wall 3527 is a retaining cavity which provides a volume to hold and position the companion element within the annular wall 3527. The containment provides volume. The compression element can be compressed into without impinging or contacting other components in the system such as the body 3506. Containment sleeve is disposed between nut 3525 and upper thrust washer 3550 and surrounds the compression element 3522. Connector 3570 passes through nose cone 3560 and forces the nose cone 3560 into engagement with the distal end 3507 of body 3506. Lower thrust washer 3552 is affixed to distal end 3507. Affixation can be achieved through barbed dog latches 3553 (see FIG. 9A) extended from the lower thrust washer towards the distal end 3507 similar to element 155 shown in FIG. 6. Keyed profiles 3560KP are provided on the nose cone 3560 back side 3561' which cooperate with matching catches 3550A-D on upper thrust washer 3550 such that they interface and rotate together as a unit. One or more washers 3520 can be provided between collar 3561 of nose cone 3560 and the lower portion of distal end 3507 of the body 3506.

Roller bearing 3551 can have a plurality of bearing elements. At least three bearing elements should be provided to ensure that no wobble can occur across the interfaces of elements 3550/3552. Fewer bearing elements may better provide for higher predetermined torque limits. Thrust washers 3550 and 3552 require no special finishing or polishing steps. Lower thrust washer 3552 may be utilized with bare machine finish on the bearing-interface surface.

Compression element 3522 is depicted as a wave spring, but may be a different element or combination of different elements. If it is a wave spring, it can be provided with shim ends to provide a full contact surface across the ends to adjacent components. Compression element 3522 can be a coil spring. Compression element 3522 can be a bushing of a compressible material, such as a nylon or neoprene. Compression element 3522 can also be a wave washer or a plurality of wave washers stacked together. Compression element 3522 could also be a stack of one or more of the types of elements described above used in combination. A wave spring is preferable in some implementations because the necessary compressive force can be provided from a shorter element than with a traditional coil spring. Further, the use of gearless bearing elements for the clutch system, rather than traditional crown gears with teeth that require vertical travel during actuations, allows for the selection of compression elements that provide high compressive force values without the need for as large of a proportional change in length due to the compressive force.

Nut 3525 may provide an upper shoulder portion 3525B having a diameter larger than the inner diameter of element 3522 and a lower neck portion 3525C having outer diameter substantially equal to an inner diameter of element 3522. One or more washers 3523 may rest on shoulder portion 3525B of nut 3525. Lower neck portion 3525C of nut 3525 may extend axially through at least a portion of compression element 3522. As depicted, nut 3525 is made from a softer material than threading 3572 of connector 3570 to allow the threading 3572 to cut threads into thread rests disposed within the internal axial bore of nut 3525. Alternatively, and preferably for higher torque implementations that may require a stronger retaining force within the nut/threading connection, nut 3525 may be made from a metal material and provided with machine-formed internal threads therein.

Internal shaft and mating connector 3570 includes a threaded end 3572 and a drive connection 3800 that interfaces with a drive socket 3562 (not shown) within the axial bore of nose cone 3560. According to aspects of some exemplary implementations, drive connection 3800 and drive socket 3562 have complementary geometries. One or more of a variety of configurations may be provided for engaging drive connection 3800 within drive socket 3562. For example drives and associated connections may include triangular, square, hexagonal, rectangular, etc. According to aspects of one or more exemplary implementations, a substantially square drive connection 3800 and drive socket 3562 provide high torque transfer capabilities. Out of a variety of drive types, experimental results demonstrated that square drives and connections were among the most successful at transferring high torque without failure. Drive connection 3800 and drive socket 3562 may have rounded corners and edges to reduce or distribute stress risers.

Internal shaft and mating connector 3570 includes a tip connection 3802 within a recess at its distal end. Tip connection 3802 is configured to receive a workpiece engaging tip. Suitable configurations for tip connection 3802 and workpiece engaging tips are disclosed in U.S. Patent Publication No. US2013/0226192 A1, which is incorporated by reference herein in its entirety.

In assembly, the thrust washers and bearing element are affixed into a drive train via the connector 3570 with a drive connection 3800 engaged into the drive socket 3562. The threading 3572 is passed through lower thrust washer, bearing element (3551), the upper thrust washer, and the compression element and threaded into the nut 3525 such that the compression element is compressed to provide force onto the other elements. The bearing element is compressed such that the upper thrust washer and lower thrust washer engage for relative rotation when a motor applies rotational force to the drive shaft. The upper thrust washer and lower thrust washer disengage when a predetermined torque limit is exceeded.

The implementations depicted in some aspects in FIGS. 8-9E are preferable over the prior art systems in FIGS. 1-2 for at least the reason that the overall dimensions of the system can be drastically reduced. For example, in one implementation, distance D1 can be approximately 1.8 inches, while distance D2 can be approximately 1.08 inches. This compares favorably with the prior art system of FIG. 1, which was roughly twice the size in distance D1 when providing comparable torque-limiting performance. Further, the simplification of the clutch elements as compared to crown gear teeth allows for incorporation of more of the tip connection components 3802 within the overall envelope of body 3506. A shorter length is highly preferable for surgeon's ease of use as it allows for more stability between a power tool and the workpiece being affixed within the surgical field. Further, more compact torque-limiting devices may be more suitable for inclusion as components within the drive-trains of other devices.

FIGS. 10A-10E depicts test data of one implementation of the in-line torque limiting device shown in FIGS. 8 and 9A-9D, beginning on page 4. Experimental testing revealed the use of a single PTFE material washer 3520 was prone to failure, due to one surface of the washer being subjected to the continuous rotation of the housing and the opposite side of the same washer being exposed to the 'stationary' shaft assembly. The washer was subjected to twisting forces with enough friction to deteriorate the PTFE washer over many rotations. Preferred implementations can utilize more durable systems for element 3520, including a delrin washer, a metal washer, or a combination of a plurality of delrin or metal washers. In some preferred implementations, a stack of three metal washers can be used for element 3520.

According to aspects of one or more exemplary implementations, various materials may be used for the components. According to some exemplary implementations, at least one of housing body, drive cap, connector mount, nut, upper shank, lower shank, or nose cone is of a plastic material or a composite including plastic. Plastic and other economical equivalents improve cost efficiency of production while providing high tensile strength, resistance to deformation, etc. Effective materials include plastics, resins, polymers, imides, fluoropolymers, thermoplastic polymers, thermosetting plastics, and the like as well as blends or mixtures thereof.

According to aspects of one or more exemplary implementations, materials and components of disposable in-line drivers of the present disclosure are resistant to sterilization, cleaning, and preparation operations. For example, drivers and parts thereof are configured to withstand sterilization by methods including radiation (e.g., gamma rays, electron beam processing), steam (e.g., autoclave), detergents, chemical (e.g., Ethylene Oxide), heat, pressure, inter alia. For example, materials may be selected according to resistance to one or more selected sterilization techniques.

While the method and apparatus have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A disposable motor powered torque-limiting driver comprising:
   a plastic cylindrical body having a fortified connector mount affixed at a proximal end and a plastic nose cone partially inserted into a distal end of the cylindrical body, the nose cone having a keyed external profile at the end inserted into the cylindrical body and a drive socket within an axial bore of the nose cone;
   a drive shaft mounted in said connector mount;
   wherein the cylindrical body contains:
      an upper thrust washer having a keyed profile that is mated to matching catches of the nose cone;
      a lower thrust washer affixed to the cylindrical body;
      a bearing element disposed between the upper thrust washer and lower thrust washer;
      a connector having a tip, a drive connection, and a threading, the connector being engaged within the drive socket of the nose cone;
      a nut having an extended shoulder portion, a lower neck portion and with internal features to engage with the threading of the connector;
      a compression element between the upper thrust washer and nut within a plastic containment configured to prevent impingement of the compression element against other system components, wherein the compression element is configured to apply a force across the upper thrust washer and the lower thrust washer to compress the bearing element;

wherein the bearing element is compressed such that the upper thrust washer and lower thrust washer engage for relative rotation when a motor applies rotational force to the drive shaft; and, wherein the upper thrust washer and lower thrust washer disengage when a predetermined torque limit is exceeded.

2. The torque-limiting driver of claim 1, further comprising:

a shoulder integral to the nut of a diameter larger than the compression element's inner diameter; and, the neck extending below said shoulder of a diameter smaller than the compression element's inner diameter.

3. The torque-limiting driver of claim 1, wherein a force provided by the compression element securely maintains the drive connection of the connector engaged within the drive socket of the nose cone.

4. The torque-limiting driver of claim 1, further comprising:

barbed dog latches extending from one side of the lower thrust washer and which mate to the distal end; and, wherein the lower thrust washer is affixed to the distal end.

5. The torque-limiting driver of claim 1, further comprising one or more washers between the nose cone and the cylindrical body.

6. The torque-limiting driver of claim 1, comprising at least one washer between the compression element and the nut.

7. The torque-limiting driver of claim 1, wherein the driver applies a torque of between about 1 N-m and about 2 N-m, at a rotational speed exceeding 250 RPM.

8. The torque-limiting driver of claim 1, wherein the driver applies a torque of between about 1 N-m and about 2 N-m, at a rotational speed exceeding 500 RPM.

9. The torque-limiting driver of claim 1, wherein the driver applies a torque of between about 1 N-m and about 2 N-m, at a rotational speed exceeding 750 RPM.

10. The torque-limiting driver of claim 1, wherein the driver applies a torque of between about 1 N-m and about 2 N-m, at a rotational speed between 150 RPM and 850 RPM.

11. The torque-limiting driver of claim 2, wherein the compression element is a spring between the upper thrust washer and nut, wherein the spring is configured to apply a force across the upper thrust washer and the lower thrust washer, and wherein the spring is connected via the threading to the nut.

* * * * *